(12) United States Patent
Taurick

(10) Patent No.: US 6,765,130 B2
(45) Date of Patent: Jul. 20, 2004

(54) INBRED CUCUMBER LINE 8D-5079

(75) Inventor: Gary Taurick, Fall River, WI (US)

(73) Assignee: Harris Moran Seed Company, Modesto, CA (US)

( * ) Notice: Subject to any disclaimer, the term of this patent is extended or adjusted under 35 U.S.C. 154(b) by 0 days.

(21) Appl. No.: 10/073,930

(22) Filed: Feb. 14, 2002

(65) Prior Publication Data

US 2003/0154521 A1 Aug. 14, 2003

(51) Int. Cl.[7] .............................. A01H 5/00; A01H 5/10; A01H 1/00; C12N 5/04
(52) U.S. Cl. ........................ 800/307; 800/260; 435/410
(58) Field of Search ................................ 800/307, 260, 800/278, 279, 265; 435/410, 430

(56) References Cited

U.S. PATENT DOCUMENTS 5,523,520 A * 6/1996 Hunsperger et al. ........ 800/200

OTHER PUBLICATIONS

Eshed et al, 1996, Genetics 143:1807–1817.*
Kraft et al, 2000, Theor. Applied. Genet. 101:323–326.*
Wehner, 1998, Hortscience 33:168–170.*
Walters et al, 1997, HortScience 32:1301–1303.*

* cited by examiner

*Primary Examiner*—Anne R. Kubelik
(74) *Attorney, Agent, or Firm*—Jondle & Associates P.C.

(57) ABSTRACT

An inbred cucumber line, designated 8D-5079, is disclosed. The invention relates to the seeds of inbred cucumber line 8D-5079, to the plants of inbred cucumber line 8D-5079 and to methods for producing a cucumber plant, either inbred or hybrid, by crossing the inbred line 8D-5079 with itself or another cucumber line. The invention further relates to methods for producing a cucumber plant containing in its genetic material one or more transgenes and to the transgenic plants produced by that method and to methods for producing other inbred cucumber lines derived from the inbred 8D-5079.

17 Claims, No Drawings

INBRED CUCUMBER LINE 8D-5079

BACKGROUND OF THE INVENTION

The present invention relates to a new and distinctive cucumber inbred line, designated 8D-5079. There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety or hybrid an improved combination of desirable traits from the parental germplasm. These important traits may include higher yield, field performance, fruit and agronomic quality such as fruit shape and length, small cavity size, flesh texture, resistance to diseases and insects, and tolerance to drought and heat.

Practically speaking, all cultivated forms of cucumber belong to the highly polymorphic species *Cucumis sativus* L. that is grown for its edible fruit. As a crop, cucumbers are grown commercially wherever environmental conditions permit the production of an economically viable yield. They can be hand or mechanically harvested. Cucumbers that are grown for fresh market, also called slicers, are generally hand harvested. Those that are to be processed are called pickles and may be hand or mechanically harvested. They are produced on trailing or climbing vines. On healthy plants there is a canopy of large, regular, three lobed leaves, in an alternate arrangement. Pickling cucumbers grown in the United States have usually blunt and angular fruits. They are white-spined and most possess dark green or medium dark green exterior color. Most slicers have slightly rounded ends and taper slightly from the stem to blossom end, although cylindrical-shaped fruits with blocky or even rounded ends are also available. Many changes that occurred with the domestication of the cucumber relate to fruit morphology, with a specialization in fruit shape and size. Slicing cucumbers are frequently sold in lengths from 6 to 10 in. and diameter varies from $1^{1/2}$ to nearly 3 in. In the United States, the principal slicer cucumber growing regions are Georgia, Florida, Michigan, California and North Carolina with nearly 42,000 acres out of a US total acreage of 57,500 acres. The main states that produce processing cucumbers are Michigan, North Carolina and Texas. Fresh cucumbers are available in the United States mainly from spring to fall. Cucumbers are consumed in many forms, generally processed for pickling types and as fresh market product for slicers. Although slicing cultivars may be processed, they generally are not acceptable substitutes for the pickling cucumbers.

*Cucumis sativus* is a member of the family Cucurbitaceae. The Cucurbitaceae is a family of about 90 genera and 700 to 760 species, mostly of the tropics. The family includes melons, pumpkins, squashes, gourds, watermelon, loofah and many weeds. The genus Cucumis, to which the cucumber and several melons belong, includes about 70 species. The cucumber is believed to be native to India or Southern Asia and has been apparently there for 3000 years.

Cucumber is distinct from other Cucumis species in that it has seven pairs of chromosomes ($2n=2x=14$) whereas most others have twelve pairs or multiple of twelve. Pollination techniques for controlled crosses in cucumbers are easy to conduct. If bees and natural pollen vectors can be excluded, the breeder need not to be concerned about preventing selfing or other pollen contamination because of the diclinous nature of cucumbers and the stickiness or adherence of pollen to its source flower. There is no wind dissemination of pollen. Pistillate flowers are receptive in the morning or up to midday on the day they open. Cucumbers have a broad range of floral morphologies, from staminate, pistillate to hermaphodite flowers, yielding several types of sex expression.

Choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of the breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested and compared to appropriate standards in environments representative of the commercial target area(s) for three years at least. The best lines are candidates for new commercial cultivars; those still deficient in a few traits are used as parents to produce new populations for further selection.

These processes, which lead to the final step of marketing and distribution, usually take from eight to 12 years from the time the first cross is made. Therefore, development of new cultivars is a time-consuming process that requires precise forward planning, efficient use of resources, and a minimum of changes in direction.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, replicated observations provide a better estimate of its genetic worth.

The goal of plant breeding is to develop new, unique and superior cucumber inbred lines and hybrids. The breeder initially selects and crosses two or more parental lines, followed by repeated selfing or sib crossing and selection, producing many new genetic combinations. The breeder can theoretically generate billions of different genetic combinations via crossing, selfing and mutations. The breeder has no direct control at the cellular level. Therefore, two breeders will never develop the same line, or even very similar lines, having the same cucumber traits.

Each year, the plant breeder selects the germplasm to advance to the next generation. This germplasm is grown under unique and different geographical, climatic and soil conditions, and further selections are then made, during and at the end of the growing season. The inbred lines that are developed are unpredictable. This unpredictability is because the breeder's selection occurs in unique environments, with no control at the DNA level (using conventional breeding procedures), and with millions of different possible genetic combinations being generated. A breeder of ordinary skill in the art cannot predict the final resulting lines he develops, except possibly in a very gross and general fashion. The same breeder cannot produce the same line twice by using the exact same original parents and the same selection techniques. This unpredictability results in the expenditure of large research monies to develop a superior new cucumber inbred line.

The development of commercial cucumber hybrids requires the development of homozygous inbred lines, the crossing of these lines, and the evaluation of the crosses. Pedigree breeding and recurrent selection breeding methods are used to develop inbred lines from breeding populations. Breeding programs combine desirable traits from two or more inbred lines or various broad-based sources into breeding pools from which inbred lines are developed by selfing and selection of desired phenotypes. The new inbreds are crossed with other inbred lines and the hybrids from these crosses are evaluated to determine which have commercial potential.

Pedigree breeding is used commonly for the improvement of self-pollinating crops or inbred lines of cross-pollinating crops. Two parents that possess favorable, complementary traits are crossed to produce an $F_1$. An $F_2$ population is produced by selfing one or several $F_1$'s or by intercrossing two $F_1$'s (sib mating). Selection of the best individuals is usually begun in the $F_2$ population; then, beginning in the $F_3$, the best individuals in the best families are selected. Replicated testing of families, or hybrid combinations involving individuals of these families, often follows in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous cultivar or inbred line that is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

Descriptions of other breeding methods that are commonly used for different traits and crops can be found in one of several reference books (e.g., "Principles of Plant Breeding" John Wiley and Son, pp. 115–161, 1960; Allard, 1960; Simmonds, 1979; Sneep et al., 1979; Fehr, 1987).

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, the grower, processor and consumer; for special advertising and marketing, altered seed and commercial production practices, and new product utilization. The testing preceding release of a new cultivar should take into consideration research and development costs as well as technical superiority of the final cultivar. For seed-propagated cultivars, it must be feasible to produce seed easily and economically.

Once the inbreds that give the best hybrid performance have been identified, the hybrid seed can be reproduced indefinitely as long as homogeneity of the inbred parents is maintained. A single-cross hybrid is produced when two inbred lines are crossed to produce the $F_1$ progeny.

Cucumber is an important and valuable field crop. Thus, a continuing goal of plant breeders is to develop stable, high yielding cucumber hybrids that are agronomically sound. The reasons for this goal are obviously to maximize the amount of fruit produced on the land used as well as to improve the fruit agronomic qualities. To accomplish this goal, the cucumber breeder must select and develop cucumber plants that have the traits that result in superior parental lines for producing hybrids.

SUMMARY OF THE INVENTION

According to the invention, there is provided a novel inbred cucumber line, designated 8D-5079. This invention thus relates to the seeds of inbred cucumber line 8D-5079, to the plants of inbred cucumber line 8D-5079 and to methods for producing a cucumber plant produced by crossing the inbred line 8D-5079 with itself or another cucumber line, and to methods for producing a cucumber plant containing in its genetic material one or more transgenes and to the transgenic cucumber plants produced by that method. This invention also relates to methods for producing other inbred cucumber lines derived from inbred cucumber line 8D-5079 and to the inbred cucumber lines derived by the use of those methods. This invention further relates to hybrid cucumber seeds and plants produced by crossing the inbred line 8D-5079 with another cucumber line.

Parts of the cucumber plant of the present invention are also provided, such as e.g., pollen obtained from an inbred plant and an ovule of the inbred plant.

In another aspect, the present invention provides regenerable cells for use in tissue culture of inbred cucumber plant 8D-5079. The tissue culture will preferably be capable of regenerating plants having the physiological and morphological characteristics of the foregoing inbred cucumber plant, and of regenerating plants having substantially the same genotype as the foregoing inbred cucumber plant. Preferably, the regenerable cells in such tissue cultures will be embryos, protoplasts, meristematic cells, callus, pollen, leaves, anthers, stems, petioles, roots, root tips, fruits, seeds, flowers or the like. Still further, the present invention provides cucumber plants regenerated from the tissue cultures of the invention.

Another objective of the invention is to provide methods for producing other inbred cucumber plants derived from inbred cucumber line 8D-5079. Inbred cucumber lines derived by the use of those methods are also part of the invention.

The invention also relates to methods for producing a cucumber plant containing in its genetic material one or more transgenes and to the transgenic cucumber plant produced by that method.

In another aspect, the present invention provides for single gene converted plants of 8D-5079. The single transferred gene may preferably be a dominant or recessive allele. Preferably, the single transferred gene will confer such trait as sex determination, herbicide resistance, insect resistance, resistance for bacterial, fungal, or viral disease, improved harvest characteristics, enhanced nutritional quality, improved agronomic quality. The single gene may be a naturally occurring cucumber gene or a transgene introduced through genetic engineering techniques.

The invention further provides methods for developing cucumber plants in a cucumber plant breeding program using plant breeding techniques including recurrent selection, backcrossing, pedigree breeding, restriction fragment length polymorphism enhanced selection, genetic marker enhanced selection and transformation. Marker loci such as restriction fragment polymorphisms or random amplified DNA have been published for many years and may be used for selection (See Pierce et al., *HortScience* (1990) 25:605–615, Wehner T., *Cucurbit Genetics Cooperative Report*, (1997) 20: 66–88 and Kennard et al., *Theorical Applied Genetics* (1994) 89:217–224). Seeds, cucumber plants, and parties thereof produced by such breeding methods are also part of the invention.

DEFINITIONS

In the description and tables that follow, a number of terms are used. In order to provide a clear and consistent understanding of the specification and claims, including the scope to be given such terms, the following definitions are provided:

Allele. The allele is any of one or more alternative forms of a gene, all of which alleles relates to one trait or characteristic. In a diploid cell or organism, the two alleles of a given gene occupy corresponding loci on a pair of homologous chromosomes.

Backcrossing. Backcrossing is a process in which a breeder repeatedly crosses hybrid progeny back to one of the parents, for example, a first generation hybrid $F_1$ with one of the parental genotype of the $F_1$ hybrid.

Essentially all the physiological and morphological characteristics. A plant having essentially all the physiological and morphological characteristics means a plant having the physiological and morphological characteristics, except for the characteristics derived from the converted gene.

Regeneration. Regeneration refers to the development of a plant from tissue culture.

Single gene converted. Single gene converted or conversion plant refers to plants which are developed by a plant breeding technique called backcrossing wherein essentially all of the desired morphological and physiological characteristics of an inbred are recovered in addition to the single gene transferred into the inbred via the backcrossing technique or via genetic engineering.

Quantitative Trait Loci (QTL) Quantitative trait loci refer to genetic loci that control to some degree numerically representable traits that are usually continuously distributed.

Cavity. As used herein, cavity refers to the center of the cucumber fruit containing seeds and associated tissues.

Monoecious plant is said of a plant having separate staminate and pistillate flowers on the same plant.

Androecious plant: is said of a plant having staminate flowers only.

Gynoecious plant: is said of a plant having pistillate flowers only.

Yield: Fresh market cucumber yield is measured either in bushels, bins or cwt (hundredweight) per acre.

Blunt ends: Blunt ends are ends of the cucumber fruits that are not tapered or rounded.

Indeterminate vine or Indeterminate Growth: Refers to apical meristem producing an unrestricted number of lateral organs; characteristic of vegetative apical meristems. (Anatomy of Seed Plants, 2nd Edition, 1977, John Wiley and Sons, page 513). The main stem of the plant continues to grow as long as the plant stays healthy, as opposed to a determinate plant, which at some point in its life cycle will stop growing longer.

Fruit quality Fruit quality characteristics for slicing cucumbers include shape, length, skin color, firmness, interior characteristics and skin texture.

Extended yield pattern: A plant having an extended yield pattern will have a vine that will continue to produce fruit over a period of time, rather than producing all the fruits at once.

Blossom scar: The blossom scar is the small mark left on the distal end of the fruit after the flower falls off.

Blossom end: The blossom end is the distal end of the fruit (the "far" end as measured from the base of the plant) where the flower blossom is located. The other end of a fruit is the stem end.

Reduced blossom end striping: Cucumber fruit normally have a striped pattern at the blossom end. The stripes are lighter color green or yellowish. 8D-5079 has a less distinct striping pattern than most other cucumbers.

DETAILED DESCRIPTION OF THE INVENTION

Inbred cucumber line 8D-5079 is a monoecious slicer cucumber with superior characteristics, and provides an excellent pollen parent line in crosses for producing first generation ($F_1$) hybrid cucumbers. Inbred cucumber line 8D-5079 is well adapted to all US regions where slicing cucumbers are usually grown (such as Georgia, Florida, Michigan, California and North Carolina), as well as Central and South American regions. Inbred cucumber line 8D-5079 produces fruit with round cross section, very dark green skin color, reduced blossom end striping, small seed cavity and small blossom scar. The yield is very high, with an extended pattern. The plant has an indeterminate growth. Inbred cucumber line 8D-5079 is resistant/tolerant to Angular Leaf Spot (*Pseudomonas lachfymans*), Anthracnose race2 (*Colletotrichum orbiculare*), Cucumber scab (*cladosporium cucumerium*), Powdery mildew (*Sphaerotheca fuliginea*) and Cucumber mosaic virus. Inbred cucumber line 8D-5079 can be used to produce hybrids having uniform dark green color, high yield and good fruit quality. Hybrids made using 8D-5079 as the pollen parent are well adapted for cucumber culture in North America, Mexico, Central America, South America and Europe. 8D-5079 might be used to produce hybrids having a maturity between 55 and 62 days.

During the development of 8D-5079, the single cross of 3998×3996 (pot numbers used in the Ferry-Morse research greenhouse in Sun Prairie, Wisconsin) was made in 1993. After this initial cross was made, progeny were self- or sib-pollinated for inbred advancement in the Wisconsin greenhouse, selecting for horticultural traits and disease resistance in every generation. Selection pressure was for monoeciousness, cylindrical fruit shape with blunt ends, fruit shape of 7.5 to 8.5 inches, dark green fruit color with reduced blossom end striping, early maturity and tolerance to Cucumber scab, Cucumber Mosaic Virus, Anthracnose, Angular Leaf Spot, and Powdery Mildew.

8D-5079 is similar to 'Marketmore76' and 'Poinsett76'. All three are slicing cucumbers, but 8D-5079 has differences in fruit color and disease tolerance. 8D-5079 is darker green than either 'Marketmore 76' and 'Poinsett 76', with reduced blossom end striping. 8D-5079 is resistant to Angular Leaf Spot and Anthracnose race 2 while 'Marketmore76' is susceptible to both diseases; 8D-5079 is resistant to Cucumber Mosaic Virus while 'Poinsett76' is susceptible.

8D-5079 is an inbred line with high yield potential, vigorous indeterminate vine and dark green fruit with cylindrical shape, blunt ends and reduced blossom end striping. Hybrid combinations results in plants which are vigorous, disease resistant and high yielding of dark green, good quality fruit that are 7.5 to 9 inches long.

Some of the criteria used to select fruits/plants in various generations include: monoeciousness, cylindrical fruit shape with blunt ends, fruit length of 7.5 to 8.5 inches, dark green fruit color with reduced blossom end striping, early maturity and tolerance to Cucumber scab, Cucumber Mosaic Virus, Anthracnose, Angular Leaf Spot, Powdery Mildew. The inbred was evaluated in numerous crosses at the Harris Moran Sun Prairie, Wisconsin Research Station and on commercial cucumber farms in North Carolina and Florida in field tests under the constant control of Harris Moran Seed Company. The inbred has proven to have a good combining ability in hybrid combinations.

The inbred line has shown uniformity and stability for the traits, within the limits of environmental influence for the traits. It has been self-pollinated a sufficient number of generations with careful attention to uniformity of plant type. The line has been increased with continued observation for uniformity. No variant traits have been observed or are expected in 8D-5079.

Inbred cucumber line 8D-5079 has the following morphologic and other characteristics (based primarily on data collected at Sun Prairie, Wis.)

VARIETY DESCRIPTION INFORMATION

Type
  Predominant usage: Slicing
  Predominant culture: Outdoor
  Area of best adaptation in the USA: Most Areas
Maturity
  55 days from seeding to market maturity
  5 days earlier than Poinsett 76
Plant
  Habit: Vine
  Growth: Indeterminate
  Sex: Monoecious
  Flower Color: Yellow
Main Stem
  Length: 16.8 cm
  Internode length: 7 cm
  Main stem: grooved
Leaf
  Length: 14.7 mm
  Width: 2.14 mm
  Petiole length: 20 cm
Fruit (at Market Maturity)
  Length: 19–21.5 cm
  Diameter at medial: 5.3 cm
  Weight: 319 gm
  Skin color: not mottled
  Dark Green blossom end stripes
  Predominant color at stem end: Dark green
  Predominant color at blossom end: Dark Green
  Shape: not necked, with ends blunt or rounded
  Stem end cross section: circular
  Medial cross section: circular
  Blossom end cross section: circular
  Skin: thick, not ribbed, tough, glossy
  Spines: white, coarse, few
  Tubercles: few, prominent
  Flavor: bitter
Fruit at Seed Harvest Maturity
  Length: 23–25 cm
  Diameter at medial: 8 cm
  Color: yellow, stripped
  Surface: smooth
  Netting: slight or none
  Fruit Set: normally with seeds
Seeds
  Number of seeds per fruit: 97
  Weight of 1000 seeds: 23 gm
Disease Resistance
  Angular leaf spot (*Pseudomonas lachrymans*): resistant
  Anthracnose race2 (*Colletotrichum orbiculare*): resistant
  Cucumber scab (*Cladosporium cucumerium*): resistant
  Powdery mildew (*Sphaerotheca fuliginea*): resistant
  Cucumber mosaic virus: resistant
  Downy Mildew (*Pseudoperonospora cubensis*): not tested but probably resistant

FURTHER EMBODIMENTS OF THE INVENTION

This invention also is directed to methods for producing a cucumber plant by crossing a first parent cucumber plant with a second parent cucumber plant wherein either the first or second parent cucumber plant is an inbred cucumber plant of the line 8D-5079. Further, both first and second parent cucumber plants can come from the inbred cucumber line 8D-5079. Still further, this invention also is directed to methods for producing an inbred cucumber line 8D-5079-derived cucumber plant by crossing inbred cucumber line 8D-5079 with a second cucumber plant and growing the progeny seed, and repeating the crossing and growing steps with the inbred cucumber line 8D-5079-derived plant from 0 to 7 times. Thus, any such methods using the inbred cucumber line 8D-5079 are part of this invention: selfing, backcrosses, hybrid production, crosses to populations, and the like. All plants produced using inbred cucumber line 8D-5079 as a parent are within the scope of this invention, including plants derived from inbred cucumber line 8D-5079. Advantageously, the inbred cucumber line is used in crosses with other, different, cucumber inbreds to produce first generation (F$_1$) cucumber hybrid seeds and plants with superior characteristics.

As used herein, the term plant includes plant cells, plant protoplasts, plant cell tissue cultures from which cucumber plants can be regenerated, plant calli, plant clumps and plant cells that are intact in plants or parts of plants, such as embryos, pollen, ovules, flowers, leaves, stalks, and the like.

As it is well known in the art, tissue culture of cucumber can be used for the in vitro regeneration of cucumber plants. Tissues cultures of various tissues of cucumber and regeneration of plants therefrom are well known and published. By way of example, tissue cultures, some comprising organs to be used to produce regenerated plants, have been described in Burza et al., *Plant Breeding*. 1995, 114: 4, 341–345, Cui Hongwen et al., *Report Cucurbit Genetics Cooperative*. 1999, 22, 5–7, Pellinen, *Angewandte Botanik*. 1997, 71: 3/4, 116–118, Kuijpers et al., *Plant Cell Tissue and Organ Culture*. 1996,46: 1, 81–83, Colijn-Hooymans et al., *Plant Cell Tissue and Organ Culture*. 1994, 39: 3, 211–217, Lou et al., *HortScience*. 1994, 29: 8, 906–909, Tabei et al., *Breeding Science*. 1994, 44: 1, 47–51, Sarmanto et al., *Plant Cell Tissue and Organ Culture* 31:3 185–193 (1992), Raharjo et al., *Reports Cucurbits Genetics Cooperative* 15, 35–39 (1992), Garcia-Sobo et al., *Reports Cucurbits Genetics Cooperative* 15, 40–44 (1992), Cade et al., *Journal of the American Society for Horticultural Science* 115:4 691–696 (1990), Chee et al., *HortScience* 25:7, 792–793 (1990), Kim et al., *HortScience* 24:4 702 (1989), Punja et al., *Plant Cell Report* 9:2 61–64 (1990). It should also be mentioned that the regeneration of the cucumber after induction of adventitious shoot buds on calli derived from cotyledons, has been described in Msikita et al., *Cucurbit Genetics Cooperative Reports*, 11: 5–7 (1988), Kim et al., *Plant Cell Tissue Organ Culture*, 12: 67–74 (1988); Wehner et al., Hort Science 16: 759–760 (1981) had previously described the induction of buds on cotyledons. Cucumber plants could be regenerated by somatic embryogenesis. These somatic embryos developed either in cell suspensions derived from calli developed from leaf explants Chee et al., Plant Cell Report 7: 274–277 (1988) or hypocotyls Rajasekaran et al., Annals of Botany, 52:P 417–420 (1983), or directly on cotyledonous Cade et al., Cucurbit Genetics Cooperative Reports 11:3–4 (1988) or leaf calli Malepszy et al., Pfanzenphysiologie, 111: 273–276 (1983). It is clear from the literature that the state of the art is such that these methods of obtaining plants are, and were, "conventional" in the sense that they are routinely used and have a very high rate of success. Thus, another aspect of this invention is to provide cells which upon growth and differentiation produce cucumber plants having the physiological and morphological characteristics of inbred cucumber line 8D-5079.

With the advent of molecular biological techniques that have allowed the isolation and characterization of genes that encode specific protein products, scientists in the field of plant biology developed a strong interest in engineering the genome of plants to contain and express foreign genes, or additional, or modified versions of native, or endogenous, genes (perhaps driven by different promoters) in order to alter the traits of a plant in a specific manner. Such foreign additional and/or modified genes are referred to herein collectively as "transgenes". Over the last fifteen to twenty years several methods for producing transgenic plants have been developed, and the present invention, in particular embodiments, also relates to transformed versions of the claimed inbred line.

Plant transformation involves the construction of an expression vector that will function in plant cells. Such a vector comprises DNA comprising a gene under control of or operatively linked to a regulatory element (for example, a promoter). The expression vector may contain one or more such operably linked gene/regulatory element combinations. The vector(s) may be in the form of a plasmid, and can be used alone or in combination with other plasmids, to provide transformed cucumber plants, using transformation methods as described below to incorporate transgenes into the genetic material of the cucumber plant(s).

Expression Vectors for Cucumber Transformation

Marker Genes—Expression vectors include at least one genetic marker, operably linked to a regulatory element (a promoter, for example) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or a herbicide, or genes that encode an altered target that is insensitive to the inhibitor. A few positive selection methods are also known in the art.

One commonly used selectable marker gene for plant transformation is the neomycin phosphotransferase II (nptII) gene, isolated from transposon Tn5, which when placed under the control of plant regulatory signals confers resistance to kanamycin. Fraley et al., *Proc. Natl. Acad. Sci. U.S.A.*, 80:4803 (1983), Ganapathi et al., *Horticulturae* 510 405–407 (2000), Raharjo et al., *Reports Cucurbit Genetics Cooperative* 19, 42–46 (1996), Nishibayashi et al., *Plant Cell Report* 15:11, 809–814 (1996). Another commonly used selectable marker gene is the hygromycin phosphotransferase gene that confers resistance to the antibiotic hygromycin. Vanden Elzen et al., *Plant Mol. Biol.*, 5:299 (1985).

Additional selectable marker genes of bacterial origin that confer resistance to antibiotics include gentamycin acetyl transferase, streptomycin phosphotransferase, aminoglycoside-3'-adenyl transferase, the bleomycin resistance determinant. Hayford et al., *Plant Physiol.* 86:1216 (1988), Jones et al., *Mol. Gen. Genet.*, 210:86 (1987), Svab et al., *Plant Mol. Biol.* 14:197 (1990<Hille et al., *Plant Mol. Biol.* 7:171 (1986). Other selectable marker genes confer resistance to herbicides such as glyphosate, glufosinate or broxynil. Comai et al., *Nature* 317:741–744 (1985), Gordon-Kamm et al., *Plant Cell* 2:603–618 (1990) and Stalker et al., *Science* 242:419–423 (1988), Ganapathi et al., *Horticulturae* 510 405–407 (2000).

Other selectable marker genes for plant transformation are not of bacterial origin. These genes include, for example, mouse dihydrofolate reductase, plant 5-enolpyruvylshikimate-3-phosphate synthase and plant acetolactate synthase. Eichholtz et al., *Somatic Cell Mol. Genet.* 13:67 (1987), Shah et al., *Science* 233:478 (1986), Charest et al., *Plant Cell Rep.* 8:643 (1990).

Another class of marker genes for plant transformation requires screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include betaglucuronidase (GUS), alpha-galactosidase, luciferase and chloramphenicol, acetyltransferase. Jefferson, R. A., *Plant Mol. Biol. Rep.* 5:387 (1987), Teeri et al., *EMBO J.* 8:343 (1989), Koncz et al., *Proc. Natl. Acad. Sci U.S.A.* 84:131 (1987), DeBlock et al., *EMBO J.* 3:1681 (1984). Sapountzakis et al., *Reports Cucurbit Genetics Cooperative* 19, 38–41 (1996), Wieczorek et al., *Plant Cell Report* 14:5, 603–610, (1995).

Recently, in vivo methods for visualizing GUS activity that do not require destruction of plant tissue have been made available. Molecular Probes publication 2908, Imagene Green™, p.1–4 (1993) and Naleway et al., *J. Cell Biol.* 115:151a (1991). However, these in vivo methods for visualizing GUS activity have not proven useful for recovery of transformed cells because of low sensitivity, high fluorescent backgrounds and limitations associated with the use of luciferase genes as selectable markers.

More recently, a gene encoding Green Fluorescent Protein (GFP) has been utilized as a marker for gene expression in prokaryotic and eukaryotic cells. Chalfie et al., *Science* 263:802 (1994). GFP and mutants of GFP may be used as screenable markers.

Promoters—Genes included in expression vectors must be driven by nucleotide sequence comprising a regulatory element, for example, a promoter. Several types of promoters are now well known in the transformation arts, as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred". Promoters which initiate transcription only in certain tissue are referred to as "tissue-specific". A "cell type" specific promoter primarily drives expression in certain cell types in one or more organs, for example, vascular cells in roots or leaves. An "inducible" promoter is a promoter which is under environmental control. Examples of environmental conditions that may effect transcription by inducible promoters include anaerobic conditions or the presence of light. Tissue-specific, tissue-preferred, cell type specific, and inducible promoters constitute the class of "non-constitutive" promoters. A "constitutive" promoter is a promoter which is active under most environmental conditions.

A. Inducible Promoters

An inducible promoter is operably linked to a gene for expression in cucumber. Optionally, the inducible promoter is operably linked to a nucleotide sequence encoding a signal sequence which is operably linked to a gene for expression in cucumber. With an inducible promoter the rate of transcription increases in response to an inducing agent.

Any inducible promoter can be used in the instant invention. See Ward et al., *Plant Mol. Biol.* 22:361–366 (1993). Exemplary inducible promoters include, but are not limited to, that from the ACEI system which responds to copper (Meft et al., *PNAS* 90:4567–4571 (1993)); In2 gene from maize which responds to benzenesulfonamide herbicide safeners (Hershey et al., *Mol. Gen Genetics* 227:229–237 (1991) and Gatz et al., *Mol. Gen. Genetics* 243:32–38 (1994)) or Tet repressor from Tn10 (Gatz et al., *Mol. Gen. Genetics* 227:229–237 (1991). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone. Schena et al., *Proc. Natl. Acad. Sci. U.S.A.* 88:0421 (1991).

B. Constitutive Promoters

A constitutive promoter is operably linked to a gene for expression in cucumber or the constitutive promoter is operably linked to a nucleotide sequence encoding a signal sequence which is operably linked to a gene for expression in cucumber.

Many different constitutive promoters can be utilized in the instant invention. Exemplary constitutive promoters include, but are not limited to, the promoters from plant viruses such as the 35S promoter from CaMV (Odell et al., *Nature* 313:810–812 (1985), Tabei et al., *Plant Cell Report* 17:3 159–164 (1997), Raharjo et al., *Plant Cell Report* 15:8, 591–596 (1996) and the promoters from such genes as rice actin (McElroy et al., *Plant Cell* 2:163–171 (1990)); ubiquitin (Christensen et al., *Plant Mol. Biol.* 12:619–632 (1989) and Christensen et al., *Plant Mol. Biol.* 18:675–689 (1992)); pEMU (Last et al., *Theor. Appl. Genet.* 81:581–588 (1991)); MAS (Velten et al., *EMBO J.* 3:2723–2730 (1984)) and maize H3 histone (Lepetit et al., *Mol. Gen. Genetics* 231:276–285 (1992) and Atanassova et al., *Plant Journal* 2 (3): 291–300 (1992)).

The ALS promoter, Xba1/Ncol fragment 5' to the Brassica napus ALS3 structural gene (or a nucleotide sequence similarity to said Xbal/Ncol fragment), represents a particularly useful constitutive promoter. See PCT application WO96/30530.

C. Tissue-Specific or Tissue-Preferred Promoters

A tissue-specific promoter is operably linked to a gene for expression in cucumber. Optionally, the tissue-specific promoter is operably linked to a nucleotide sequence encoding a signal sequence which is operably linked to a gene for expression in cucumber. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter, such as that from the phaseolin gene (Murai et al., *Science* 23:476–482 (1983) and Sengupta-Gopalan et al., *Proc. Natl. Acad. Sci. U.S.A.* 82:3320–3324 (1985)); a leaf-specific and light-induced promoter such as that from cab or rubisco (Simpson et al., *EMBO J.* 4(11):2723–2729 (1985) and Timko et al., *Nature* 318:579–582 (1985)); an anther-specific promoter such as that from LAT52 (Twell et al., *Mol. Gen. Genetics* 217:240–245 (1989)); a pollen-specific promoter such as that from Zm13 (Guerrero et al., *Mol. Gen. Genetics* 244:161–168 (1993)) or a microspore-preferred promoter such as that from apg (Twell et al., *Sex. Plant Reprod.* 6:217–224 (1993).

Signal Sequences for Targeting Proteins to Subcellular Compartments

Transport of protein produced by transgenes to a subcellular compartment such as the chloroplast, vacuole, peroxisome, glyoxysome, cell wall or mitochondroin or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized.

The presence of a signal sequence directs a polypeptide to either an intracellular organelle or subcellular compartment or for secretion to the apoplast. Many signal sequences are known in the art. See, for example Becker et al., *Plant Mol. Biol.* 20:49 (1992), Close, P. S., Master's Thesis, Iowa State University (1993), Knox, C., et al., "Structure and Organization of Two Divergent Alpha-Amylase Genes from Barley", Plant Mol. Biol. 9:3–17 (1987), Lerner et al., *Plant Physiol.* 91:124–129 (1989), Fontes et al., *Plant Cell* 3:483–496 (1991), Matsuoka et al., *Proc. Natl. Acad. Sci.* 88:834 (1991), Gould et al., *J. Cell. Biol.* 108:1657 (1989), Creissen et al., *Plant J.* 2:129 (1991), Kalderon, et al., A short amino acid sequence able to specify nuclear location, *Cell* 39:499–509 (1984), Steifel, et al., Expression of a maize cell wall hydroxyproline-rich glycoprotein gene in early leaf and root vascular differentiation, *Plant Cell* 2:785–793 (1990).

Foreign Protein Genes and Agronomic Genes

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, *Anal. Biochem.* 114:92–6 (1981).

According to a preferred embodiment, the transgenic plant provided for commercial production of foreign protein is cucumber. In another preferred embodiment, the biomass of interest is seed. For the relatively small number of transgenic plants that show higher levels of expression, a genetic map can be generated, primarily via conventional RFLP, PCR and SSR analysis, which identifies the approximate chromosomal location of the integrated DNA molecule. For exemplary methodologies in this regard, see Glick and Thompson, Methods in Plant Molecular Biology and Biotechnology CRC Press, Boca Raton 269:284 (1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR and sequencing, all of which are conventional techniques.

Likewise, by means of the present invention, agronomic genes can be expressed in transformed plants. More particularly, plants can be genetically engineered to express various phenotypes of agronomic interest. Exemplary genes implicated in this regard include, but are not limited to, those categorized below:

1. Genes That Confer Resistance to Pests or Disease and That Encode

A. Plant disease resistance genes. Plant defenses are often activated by specific interaction between the product of a disease resistance gene (R) in the plant and the product of a corresponding avirulence (Avr) gene in the pathogen. A plant inbred line can be transformed with cloned resistance gene to engineer plants that are resistant to specific pathogen strains. See, for example Jones et al., *Science* 266:789 (1994) (cloning of the tomato Cf-9 gene for resistance to *Cladosporium fulvum*); Martin et al., *Science* 262:1432 (1993) (tomato Pto gene for resistance to *Pseudomonas syringae* pv. Tomato encodes a protein kinase); Mindrinos et al., *Cell* 78:1089 (1994) (Arabidopsis RSP2 gene for resistance to *Pseudomonas syringae*).

B. A *Bacillus thuringiensis* protein, a derivative thereof or a synthetic polypeptide modeled thereon. See, for example, Geiser et al., *Gene* 48:109 (1986), who disclose the cloning and nucleotide sequence of a Bt ä-endotoxin gene. Moreover, DNA molecules encoding ä-endotoxin genes can be purchased from American Type Culture Collection, Manassas, Va., for example, under ATCC Accession Nos. 40098, 67136, 31995 and 31998.

C. A lectin. See, for example, the disclose by Van Damme et al., *Plant Molec. Biol.* 24:25 (1994), who disclose the nucleotide sequences of several *Clivia miniata* mannose-binding lectin genes.

D. A gene coding for the coat protein of the Cucumber Mosaic Comovirus (CMV), see Nishibayashi et al., *Theorical and Applied Genetics*. 1996, 93: 5/6, 672–678, which once expressed in the plant allows it to be resistant to the CMV E. An enzyme inhibitor, for example, a protease or proteinase inhibitor or an amylase inhibitor. See, for example, Abe et al., *J. Biol. Chem.* 262:16793 (1987) (nucleotide sequence of rice cysteine proteinase inhibitor), Huub et al., *Plant Molec. Biol.* 21:985 (1993) (nucleotide sequence of CDNA encoding tobacco proteinase inhibitor I), Sumitani et al., *Biosci. Biotech. Biochem.* 57:1243 (1993) (nucleotide sequence of *Streptomyces nitrosporeus* ä-amylase inhibitor).

F. An insect-specific hormone or pheromone such as an ecdysteroid and juvenile hormone, a variant thereof, a mimetic based thereon, or an antagonist or agonist thereof. See, for example, the disclosure by Hammock et al., *Nature* 344:458 (1990), of baculovirus expression of cloned juvenile hormone esterase, an inactivator of juvenile hormone.

G. An insect-specific peptide or neuropeptide which, upon expression, disrupts the physiology of the affected pest. For example, see the disclosures of Regan, *J. Biol. Chem.* 269:9 (1994) (expression cloning yields DNA coding for insect diuretic hormone receptor), and Pratt et al., *Biochem. Biophys. Res. Comm.* 163:1243 (1989) (an allostatin is identified in Diploptera puntata). See also U.S. Pat. No. 5,266,317 to Tomalski et al., who disclose genes encoding insect-specific, paralytic neurotoxins.

H. An insect-specific venom produced in nature by a snake, a wasp, etc. For example, see Pang et al., *Gene* 116:165 (1992), for disclosure of heterologous expression in plants of a gene coding for a scorpion insectotoxic peptide.

I. An enzyme responsible for a hyper accumulation of a monterpene, a sesquiterpene, a steroid, hydroxamic acid, a phenylpropanoid derivative or another non-protein molecule with insecticidal activity.

J. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott et al., which discloses the nucleotide sequence of a callase gene. DNA molecules which contain chitinase-encoding sequences can be obtained, for example, from the ATCC under Accession Nos. 39637 and 67152. See also Kramer et al., *Insect Biochem. Molec. Biol.* 23:691 (1993), who teach the nucleotide sequence of a cDNA encoding tobacco hookworm chitinase, and Kawalleck et al., *Plant Molec. Biol.* 21:673

(1993), who provide the nucleotide sequence of the parsley ubi4-2 polyubiquitin gene.

K. A molecule that stimulates signal transduction. For example, see the disclosure by Botella et al., *Plant Molec. Biol.* 24:757 (1994), of nucleotide sequences for mung bean calmodulin cDNA clones, and Griess et al., *Plant Physiol.* 104:1467 (1994), who provide the nucleotide sequence of a maize calmodulin cDNA clone.

L. A hydrophobic moment peptide. See PCT application WO95/16776 (disclosure of peptide derivatives of Tachyplesin which inhibit fungal plant pathogens) and PCT application WO95/18855 (teaches synthetic antimicrobial peptides that confer disease resistance), the respective contents of which are hereby incorporated by reference.

M. A membrane permease, a channel former or a channel blocker. For example, see the disclosure of Jaynes et al., *Plant Sci* 89:43 (1993), of heterologous expression of a cecropin-â, lytic peptide analog to render transgenic tobacco plants resistant to *Pseudomonas solanacearum*.

N. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., *Ann. rev. Phytopathol.* 28:451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

O. An insect-specific antibody or an immunotoxin derived therefrom. Thus, an antibody targeted to a critical metabolic function in the insect gut would inactivate an affected enzyme, killing the insect. Cf. Taylor et al., Abstract #497, Seventh Int'l Symposium on Molecular Plant-Microbe Interactions (Edinburgh, Scotland) (1994) (enzymatic inactivation in transgenic tobacco via production of single-chain antibody fragments).

P. A virus-specific antibody. See, for example, Tavladoraki et al., *Nature* 366:469 (1993), who show that transgenic plants expressing recombinant antibody genes are protected from virus attack.

Q. A developmental-arrestive protein produced in nature by a pathogen or a parasite. Thus, fungal endo á-1, 4-D-polygalacturonases facilitate fungal colonization and plant nutrient release by solubilizing plant cell wall homo-á-1,4-D-galacturonase. See Lamb et al., *Bio/Technology* 10:1436 (1992). The cloning and characterization of a gene which encodes a bean endopolygalacturonase-inhibiting protein is described by Toubart et al., *Plant J.* 2:367 (1992).

R. A development-arrestive protein produced in nature by a plant. For example, Logemann et al., *Bioi/Technology* 10:305 (1992), have shown that transgenic plants expressing the barley ribosome-inactivating gene have an increased resistance to fungal disease.

S. A rice chitinase gene that, upon introduction into the cucumber enhance its resistance to gray mold (*Botrytis cinera*) fungal infection. See for example Tabei et al., *Plant Cell Report.* 1997,17: 2,159–164.

2. Genes that Confer Resistance to a Herbicide, for Example

A. A herbicide that inhibits the growing point or meristem, such as an imidazalinone or a sulfonylurea. Exemplary genes in this category code for mutant ALS and AHAS enzyme as described, for example, by Lee et al., *EMBO J.* 7:1241 (1988), and Miki et al., *Theor. Appl. Genet.* 80:449 (1990), respectively.

B. Glyphosate (resistance impaired by mutant 5-enolpyruvl-3-phosphikimate synthase (EPSP) and aroA genes, respectively) and other phosphono compounds such as glufosinate (phosphinothricin acetyl transferase, PAT and *Streptomyces hygroscopicus* phosphinothricin-acetyl transferase, bar, genes), and pyridinoxy or phenoxy propionic acids and cycloshexones (ACCase inhibitor-encoding genes). See, for example, U.S. Pat. No. 4,940,835 to Shah, et al., which discloses the nucleotide sequence of a form of EPSP which can confer glyphosate resistance. A DNA molecule encoding a mutant aroA gene can be obtained under ATCC accession number 39256, and the nucleotide sequence of the mutant gene is disclosed in U.S. Pat. No. 4,769,061 to Comai. European patent application No. 0 333 033 to Kumada et al., and U.S. Pat. No. 4,975,374 to Goodman et al., disclose nucleotide sequences of glutamine synthetase genes which confer resistance to herbicides such as L-phosphinothricin. The nucleotide sequence of a phosphinothricin-acetyl-transferase gene is provided in European application No. 0 242 246 to Leemans et al., DeGreef et al., *Bio/Technology* 7:61 (1989), describe the production of transgenic plants that express chimeric bar genes coding for phosphinothricin acetyl transferase activity. Exemplary of genes conferring resistance to phenoxy propionic acids and cycloshexones, such as sethoxydim and haloxyfop are the Acc1-S1, Accl-S2 and Accl-S3 genes described by Marshall et al., *Theor. Appl. Genet.* 83:435 (1992).

C. A herbicide that inhibits photosynthesis, such as a triazine (psbA and gs+ genes) and a benzonitrile (nitrilase gene). Przibilla et al., *Plant Cell* 3:169 (1991), describe the transformation of Chlamydomonas with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes et al., *Biochem. J.* 285:173 (1992).

3. Genes that Confer or Contribute to a Value-Added Trait, Such as

A. Increased level of superoxide dismutase by transforming a plant with a superoxide dismutase gene derived from cassaya as described in U.S. Pat. No. 6,084,152.

B. Increased level of trehalose by transforming the plant with structural genes for trehalose synthase as suggered in U.S. Pat. No. 5,792,921, therefore increasing the resistance of the plant to water depravation stress.

C. Over expression of phytochrome by transforming plants with a sequence coding for a phytochrome polypeptide as suggested in U.S. Pat. No. 5,268,526 and that may change growth and morphological characteristics such as increased shade tolerance and darker green color.

Methods for Cucumber Transformation

Numerous methods for plant transformation have been developed, including biological and physical, plant transformation protocols. See, for example, Miki et al., "Procedures for Introducing Foreign DNA into Plants" in *Methods in Plant Molecular Biology and Biotechnology*, Glick B. R. and Thompson, J. E. Eds. (CRC Press, Inc., Boca Raton, 1993) pages 67–88. In addition, expression vectors and in vitro culture methods for plant cell or tissue transformation and regeneration of plants are available. See, for example, Gruber et al., "Vectors for Plant Transformation" in *Methods in Plant Molecular Biology and Biotechnology*, Glick B. R. and Thompson, J. E. Eds. (CRC Press, Inc., Boca Raton, 1993) pages 89–119.

A. Agrobacterium-Mediated Transformation

One method for introducing an expression vector into plants is based on the natural transformation system of Agrobacterium. See, for example, Ganapathi et al., *Acta Horticulturae*. 2000, 510, 405–407, Raharjo et al., *Plant Cell Report*. 1996, 15: 8, 591–596, Nishibayashi et al., *Plant Cell Report*. 1996, 15: 11, 809–814, Mark van der F et al., *Report Cucurbit Genetics Cooperative*. 1989, #12, 35–36. *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., *Crit. Rev. Plant Sci.* 10:1 (1991). Descriptions of Agrobacterium vector systems and methods for Agrobacterium-mediated gene transfer are provided by Gruber et al., supra, Miki et al., supra, and Moloney et al., *Plant Cell Reports* 8:238 (1989). See also, U.S. Pat. No. 6,198,022 issued Mar. 6, 2001.

B. Direct Gene Transfer

Despite the fact the host range for Agrobacterium-mediated transformation is broad, some major cereal crop or vegetable species and gymnosperms have generally been recalcitrant to this mode of gene transfer, even though some success has recently been achieved in rice and corn. Hiei et al., *The Plant Journal* 6:271–282 (1994) and U.S. Pat. No. 5,591,616 issued Jan. 7, 1997. Several methods of plant transformation, collectively referred to as direct gene transfer, have been developed as an alternative to Agrobacterium-mediated transformation.

A generally applicable method of plant transformation is microprojectile-mediated transformation wherein DNA is carried on the surface of microprojectiles measuring 1 to 4 lm. The expression vector is introduced into plant tissues with a biolistic device that accelerates the microprojectiles to speeds of 300 to 600 m/s which is sufficient to penetrate plant cell walls and membranes. Sanford et al., *Part. Sci. Technol.* 5:27 (1987), Sanford, J. C., *Trends Biotech.* 6:299 (1988), Klein et al., *Bio/Technology* 6:559–563 (1988), Sanford, J. C., *Physiol Plant* 7:206 (1990), Klein et al., *Biotechnology* 10:268 (1992). See also Schulze et al., *Plant Science Limerick*. 1995,112: 2,197–206, Chee et al., *Gene*. 1992. 118: 2, 255–260, Komada et al., *Transgenic Research*. 1993, 2:3,147–152.

Another method for physical delivery of DNA to plants is sonication of target cells. Zhang et al., *Bio/Technology* 9:996 (1991). Alternatively, liposome or spheroplast fusion have been used to introduce expression vectors into plants. Deshayes et al., *EMBO J*., 4:2731 (1985), Christou et al., *Proc Natl. Acad. Sci. U.S.A.* 84:3962 (1987). Direct uptake of DNA into protoplasts using $CaCl_2$ precipitation, polyvinyl alcohol or poly-L-omithine have also been reported. Hain et al., *Mol. Gen. Genet*. 199:161 (1985) and Draper et al., *Plant Cell Physiol*. 23:451 (1982). Electroporation of protoplasts and whole cells and tissues have also been described. Donn et al., In Abstracts of VIIth International Congress on Plant Cell and Tissue Culture IAPTC, A2-38, p 53 (1990); D'Halluin et al., *Plant Cell* 4:1495–1505 (1992) and Spencer et al., *Plant Mol. Biol*. 24:51–61 (1994). See also Burza et al., *Journal of Applied Genetics*. 1995, 36: 1, 1–10.

Following transformation of cucumber target tissues, expression of the above-described selectable marker genes allows for preferential selection of transformed cells, tissues and/or plants, using regeneration and selection methods now well known in the art.

The foregoing methods for transformation would typically be used for producing a transgenic inbred line. The transgenic inbred line could then be crossed, with another (non-transformed or transformed) inbred line, in order to produce a new transgenic inbred line. Alternatively, a genetic trait which has been engineered into a particular cucumber line using the foregoing transformation techniques could be moved into another line using traditional backcrossing techniques that are well known in the plant breeding arts. For example, a backcrossing approach could be used to move an engineered trait from a public, non-elite inbred line into an elite inbred line, or from an inbred line containing a foreign gene in its genome into an inbred line or lines which do not contain that gene. As used herein, "crossing" can refer to a simple X by Y cross, or the process of backcrossing, depending on the context.

When the term inbred cucumber plant is used in the context of the present invention, this also includes any single gene conversions of that inbred. The term single gene converted plant as used herein refers to those cucumber plants which are developed by a plant breeding technique called backcrossing wherein essentially all of the desired morphological and physiological characteristics of an inbred are recovered in addition to the single gene transferred into the inbred via the backcrossing technique. Backcrossing methods can be used with the present invention to improve or introduce a characteristic into the inbred. The term backcrossing as used herein refers to the repeated crossing of a hybrid progeny back to one of the parental cucumber plants for that inbred. The parental cucumber plant which contributes the gene for the desired characteristic is termed the nonrecurrent or donor parent. This terminology refers to the fact that the nonrecurrent parent is used one time in the backcross protocol and therefore does not recur. The parental cucumber plant to which the gene or genes from the nonrecurrent parent are transferred is known as the recurrent parent as it is used for several rounds in the backcrossing protocol (Poehlman & Sleper, 1994; Fehr, 1987). In a typical backcross protocol, the original inbred of interest (recurrent parent) is crossed to a second inbred (nonrecurrent parent) that carries the single gene of interest to be transferred. The resulting progeny from this cross are then crossed again to the recurrent parent and the process is repeated until a cucumber plant is obtained wherein essentially all of the desired morphological and physiological characteristics of the recurrent parent are recovered in the converted plant, in addition to the single transferred gene from the nonrecurrent parent.

The selection of a suitable recurrent parent is an important step for a successful backcrossing procedure. The goal of a backcross protocol is to alter or substitute a single trait or characteristic in the original inbred. To accomplish this, a single gene of the recurrent inbred is modified or substituted with the desired gene from the nonrecurrent parent, while retaining essentially all of the rest of the desired genetic, and therefore the desired physiological and morphological, constitution of the original inbred. The choice of the particular nonrecurrent parent will depend on the purpose of the backcross, one of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many single gene traits have been identified that are not regularly selected for in the development of a new inbred but that can be improved by backcrossing techniques. Single gene traits may or may not be transgenic, examples of these traits include but are not limited herbicide resistance, resistance for bacterial, fungal, or viral disease (Cmv resistance gene), insect resistance (Argene), enhanced nutritional quality, enhanced agronomic qualities such as parthenocarpy (gene Pc), bitterness (plants with the bi gene that lacks cucurbitacins), yield stability and yield enhancement. Some traits such as sex determination may be regulated by single genes working together such as genes M, a and Acr, also known as gene F. These genes are generally inherited through the nucleus.

TABLES

In the tables that follow, the traits and characteristics of inbred cucumber 8D-5079 are given compared to other inbreds. The data collected are presented for key characteristics and traits. 8D-5079 was tested in hybrid combinations at numerous locations, with two or three replications per location. Information about these hybrids, as compared to several check hybrids is presented.

Table 1

Column 1 shows the hybrid containing 8D-5079 as a parent, as well as check hybrids.

The yield (Yield) in cwt (hundred weight per acre) per acre of total marketable fruit is shown in column 2.

The percentage of non-marketable fruits (% culls) is shown in column 3.

Earliness ranked from the first two harvests is shown in column 4. Earliness refers to the weight of the fruit in the first two harvests. The varieties were ranked from the one with the most fruit in the first two harvests to the one with the least fruit in the first two harvests.

The fruit quality, which is a subjective evaluation where 1=poor and 9=excellent, is shown in column 5.

TABLE 1

Overall Comparisons
8D5079 vs. check hybrids
Location: 2000 at NCSU trials Locations

| Hybrid | Yield | % Culls | Earliness | Fruit Quality |
|---|---|---|---|---|
| W83049*8D5079 | 254 | 17 | 2 | 7.2 |
| General Lee | 228 | 14 | 12 | 7.1 |
| Dasher II | 211 | 16 | 14 | 6.3 |

Table 2

Column 1 shows the hybrid containing 8D-5079 as a parent, as well as check hybrids The yield (Yield) in number of marketable fruit per plant is shown in column 2.

The percentage of non-marketable (% culls) is shown in column 3.

The fruit color, which is a subjective evaluation where 1=light color and 5=dark color is shown in column 4.

The fruit length, measured in inches is shown in column 5.

TABLE 2

Overall Comparisons
8D5079 vs. check hybrids
Location: 2000 at Jupiter FL Locations

| Hybrid | Yield | % Culls | Fruit Color | Fruit Length |
|---|---|---|---|---|
| W83049*8D5079 | 3.06 | 16.8 | 4.0 | 8.50 |
| General Lee | 2.94 | 24.4 | 3.5 | 8.50 |
| Dasher II | 2.46 | 17.0 | 3.5 | 8.75 |

Table 3 and 4

Column 1 shows the hybrid containing 8D-5079 as a parent, as well as check hybrids The yield (Yield) in number of marketable fruit per plant is shown in column 2.

The percentage of non-marketable (% culls) is shown in column 3.

The fruit color, which is a subjective evaluation where 1=light color and 5=dark color is shown in column 4.

The fruit length, measured in centimeters is shown in column 5.

TABLE 3

Overall Comparisons
8D5079 vs. check hybrids
Location: 2000 at Faison, NC Locations

| Hybrid | Yield | % Culls | Fruit Color | Fruit Length |
|---|---|---|---|---|
| W83049*8D5079 | 3.13 | 26.6 | 3.8 | 17.5–22.0 |
| General Lee | 3.09 | 30.9 | 2.9 | 18.0–23.0 |
| Dasher II | 3.24 | 35.5 | 2.8 | 17.0–23.0 |

TABLE 4

Overall Comparisons
8D5079 vs. check hybrids
Location: 2000 at NCSU trial Locations

| Hybrid | Yield | % Culls | Fruit Color | Fruit Length |
|---|---|---|---|---|
| W83049*8D5079 | 3.78 | 23.3 | 3.3 | 20.0–23.5 |
| General Lee | 2.89 | 20.6 | 2.6 | 19.0–23.0 |
| Dasher II | 3.71 | 25.0 | 2.4 | 18.5–23.5 |

DEPOSIT INFORMATION

A deposit of the inbred cucumber 8D-5079 and hybrid W83049*8D-5079 of this invention is maintained by Harris Moran Seed Company, Sun Prairie Research Station, 1677 Muller Road, P.O. Box 392, Sun Prairie, Wis. 53590. Access to this deposit will be available during the pendency of this application to persons determined by the Commissioner of Patent and Trademarks to be entitled thereto under 37 CRF 1.14 and 35 USC 122. Upon allowance of any claims in this application, all restrictions on the availability to the public of the variety will be irrevocably removed by affording access to a deposit of at least 2,500 seeds of the same variety with the American Type Culture Collection (ATCC), 10801 University Boulevard, Manassas, Va. 20110.

Although the foregoing invention has been described in some detail by way of illustration and example for purposes of clarity and understanding. However, it will be obvious that certain changes and modifications such as single gene modifications and mutations, somaclonal variants, variant individuals selected from large populations of the plants of the instant inbred and the like may be practiced within the scope of the invention, as limited only by the scope of the appended claims.

What is claimed is:

1. An inbred cucumber seed designated 8D-5079, wherein a sample of said seed has been deposited under ATCC Accession No. PTA-5897.

2. A cucumber plant, or parts thereof, produced by growing the seed of claim 1.

3. Pollen of the plant of claim 2.

4. An ovule or ovules of the plant of claim 2.

5. A cucumber plant, or parts thereof, having all of the physiological and morphological characteristics of the cucumber plant of claim 2.

6. A tissue culture of regenerable cells of a cucumber plant of variety 8D-5079, wherein the tissue culture regenerates plants having all the morphological and physiological characteristics of cucumber line 8D-5079, representative seeds having been deposited under ATCC Accession number PTA-5897.

7. The tissue culture of claim 6, wherein the cells are isolated from a plant part selected from the group consisting of embryos, meristems, pollen, leaves, anthers, stems, petioles, roots, root tips, fruits, flowers, cotyledons, and hypocotyls.

8. Protoplast or callus derived from cells isolated from a plant part selected from the group consisting of embryos, meristems, pollen, leaves, anthers, stems, petioles, roots, root tips, fruits, flowers, cotyledons and hypocotyls, wherein the plant part is isolated from the plant of claim 2.

9. A cucumber plant regenerated from the tissue culture of claim 6, wherein the plant expresses all the morphological and physiological characteristics of inbred cucumber line 8D-5079, representative seeds having been deposited under ATCC number PTA-5897.

10. A method for producing a hybrid cucumber seed wherein the method comprises crossing a first inbred parent cucumber plant with a second inbred parent cucumber plant and harvesting the resultant hybrid cucumber seed, wherein said first or second parent cucumber plant is the cucumber plant of claim 2.

11. A method of producing an herbicide resistant cucumber plant wherein the method comprises transforming the cucumber plant of claim 2 with a transgene that confers herbicide resistance.

12. An herbicide resistant cucumber plant produced by the method of claim 11.

13. A method of producing an insect resistant cucumber plant wherein the method comprises transforming the cucumber plant of claim 2 with a transgene that confers insect resistance.

14. An insect resistant cucumber plant produced by the method of claim 13.

15. A method of producing a disease resistant cucumber plant comprising transforming the cucumber plant of claim 2 with a transgene that confers disease resistance.

16. A disease resistant cucumber plant produced by the method of claim 15.

17. A hybrid cucumber seed designated W83049*8D-5079, representative seed having been deposited under ATCC Accession number PTA-5928, or a hybrid W83049*8D-5079 plant produced by growing the seed.

* * * * *